(12) United States Patent
Buck

(10) Patent No.: US 6,858,215 B2
(45) Date of Patent: Feb. 22, 2005

(54) COMPOSITIONS AND METHODS FOR SOFTENING, THINNING AND REMOVING HYPERKERATOTIC TISSUE

(75) Inventor: Carol J. Buck, 33 Witherspoon St., Suite 200, Princeton, NJ (US) 08542

(73) Assignee: Carol J. Buck, Princeton, NJ (US)

(*) Notice: Subject to any disclaimer, the term of this patent is extended or adjusted under 35 U.S.C. 154(b) by 169 days.

(21) Appl. No.: 10/171,602

(22) Filed: Jun. 14, 2002

(65) Prior Publication Data

US 2003/0232042 A1 Dec. 18, 2003

(51) Int. Cl.⁷ ................................................. A61K 7/00
(52) U.S. Cl. ................... 424/401; 424/61; 424/94.1; 424/94.2
(58) Field of Search .................. 424/401, 61, 94.1, 424/94.2

(56) References Cited

U.S. PATENT DOCUMENTS

| | | | |
|---|---|---|---|
| 2,729,586 A | 1/1956 | Peck | 167/65 |
| 5,091,171 A | 2/1992 | Yu et al. | 424/642 |
| 5,213,978 A * | 5/1993 | Holland | 435/220 |
| 5,462,714 A | 10/1995 | Talwalker et al. | 422/37 |
| 6,416,769 B1 * | 7/2002 | Vromen | 424/401 |
| 6,569,437 B1 * | 5/2003 | Bishop et al. | 424/401 |

FOREIGN PATENT DOCUMENTS

| | | |
|---|---|---|
| DE | 195 36 423 A1 | 4/1996 |
| EP | 0 742 004 A2 | 11/1996 |
| EP | 0 755 676 A1 | 1/1997 |
| GB | 745179 | 8/1953 |
| WO | WO 87/04617 | 8/1987 |
| WO | WO 96/11572 | 4/1996 |
| WO | WO 97/17953 | 5/1997 |
| WO | WO 97/46231 | 12/1997 |
| WO | WO 99/20250 | 4/1999 |

OTHER PUBLICATIONS

Abstract: XP–002229542 AB–J63083026 Drug for dermatosis comprises Zn undecylenate.
Abstract: XP–002229541 AB–J03157311 Cosmetic material contains at least one of vitamin E drivs. Of succinic . . .
Abstract: XP–002229540 Treatment of Acne Vulgaris and Acne Conglobata with 20 percent adipic acid cream.
Article XP–002070145 Therapeutics for the Clinician A double–blind, vehicle–controlled study of the safety and efficacy of fungoid.
European Search Report relating to 99905970.2–1215/US9903169 dated Feb. 20, 2003.
European Search Report relating to 99905970.2 dated Jun. 23, 2003.

* cited by examiner

Primary Examiner—Thurman K. Page
Assistant Examiner—Konata M George
(74) Attorney, Agent, or Firm—Kaplan & Gilman, LLP

(57) ABSTRACT

Novel compositions and methods for treatment of hyperkeratotic mammalian tissue are disclosed employing proteolytic enzymes originally developed for the hydrolysis of food-related proteins and currently commonly used as food grade meat tenderizers and flavor enhancers. The compositions containing these proteinases soften, thin and exfoliate hyperkeratotic formations on the skin, including calluses, corns, dry, scaling/flaking skin and keratoses without harming surrounding tissue by selective lysing of hyperkeratotic tissue. Such enzymes accomplish this by lysing only the 10-end peptide bonds of keratin protein, the dominant protein component of hyperkeratotic skin.

23 Claims, 6 Drawing Sheets

Influence of pH on the activity of Alcalase.

Enzyme concentration: 0.06 AU/litre
Temperature: 60°C
Method: Modified Anson/ Hemoglobin analysis
Reaction time: 10 minutes Fig. 1. Influence of pH on the activity of Alcalase.

Enzyme concentration: 0.06 AU/litre
Temperature: 60°C
Method: Modified Anson/ Hemoglobin analysis
Reaction time: 10 minutes Fig. 2. Influence of temperature on the activity of Alcalase.

Enzyme concentration: 0.06 U/litre
PH: 8.0
Method: Modified Anson/ Hemoglobin analysis
Reaction time: 10 minutes Fig. 3. The productivity of Alcalase 2.4 L measured at various Temperatures on whey and soy protein.

Protein %:                          8%
Enzyme dosage (on protein):         0.51%
PH:                                 8.0
Reaction:                           4 hours Fig. 4. Influence of pH on the activity of Flavourzyme.

Substrate:                8% soy protein isolate
Enzyme conc.:             33 LAPU/g protein
Temperature:     50°C
Method:                   TNBS Fig. 5. Influence of temperature on the activity of Flavourzyme.

Substrate:       8% soy protein isolate
Enzyme conc.:    33 LAPU/g protein
pH:              7.0
Method:          TNBS

BEFORE TREATMENT

AFTER 14 DAYS OF TREATMENT
EMPLOYING COMPOSITION FORMULA 1

BEFORE TREATMENT

AFTER 10 DAYS OF TREATMENT
EMPLOYING FORMULA 1

US 6,858,215 B2

COMPOSITIONS AND METHODS FOR SOFTENING, THINNING AND REMOVING HYPERKERATOTIC TISSUE

FIELD OF THE INVENTION

The present invention relates to compositions and the use thereof of proteolytic enzymes developed for the hydrolysis of food-related proteins for treatment of conditions associated with hyperkeratotic mammalian tissue.

BACKGROUND

Hyperkeratotic tissue in mammals and the conditions arising therefrom result from abnormal processes within the skin. The top layer of skin, known as the stratum corneum, is composed primarily of cells that are dehydrated keratin protein. In a normal process called keratinization, epidermal cells are gradually pushed to the surface by underlying dermis cells where they exfoliate. In abnormal processes, i.e., when these cells do not exfoliate, they accumulate on the surface to form hyperkeratotic tissue causing discomfort. Hyperkeratotic tissue in mammals includes tylomas (calluses and fissures), helomas (corns), keratoses (papules), and dry skin scales and flakes. Common methods for managing hyperkeratinized tissue are the application of acids in lotion or cream carriers, moisturizing creams or lotions or mechanical scraping. Acids and scraping are disadvantageous because they tend to irritate normal epidermis and moisturizing creams are not effective in reducing hyperkeratotic tissue density.

Calluses and corns, usually found on the feet and hands, are thickened areas of normal skin which have formed to protect underlying bone from excessive weight bearing, pressure or friction. Foot callus appears most commonly on the sole and heel. Hand callus typically forms on the pads of the palm where pressure is most commonly exerted in handling tools and objects. When a callus deposits dead cells at its epicenter, it becomes a corn (heloma), a painful, conical hyperkeratosis. Corns are usually found over toe joints and between the toes and are typically caused by hammertoe, bone spurs or ill-fitting footwear impinging against skin. Calluses and corns cause walking discomfort and are commonly treated by rubbing off the hardened skin with a pumice stone or other scraping device, applying salicylic acid, or, if severe, by bone surgery to correct the underlying pressure point. Salicylic acid is effective for the removal of callus and corns but presents the risk of harming adjacent healthy tissue which is also exfoliated. Salicylic acid is also not recommended for use by the elderly with thinned skin, diabetics or by those with poor circulation or compromised immune systems, as the acid can result in open lesions which are then subject to infection.

Dry skin is a normal consequence of aging and is aggravated by cold, dry or windy climatic conditions. Treatment unusually involves the use of moisturizers after bathing, including petrolatum, lanolin, urea, alpha hydroxy acids, lactic acid or ammonium lactate to reduce scaling and help the skin hold water.

SUMMARY OF THE INVENTION

The present invention is directed to novel compositions and methods for treatment of hyperkeratotic mammalian tissue employing proteolytic enzymes originally developed for the hydrolysis of food-related proteins and currently commonly used as food grade meat tenderizers and flavor enhancers. Surprisingly, the inventor has discovered that these novel compositions containing these proteinases safely soften, thin and exfoliate hyperkeratotic formations on the skin, including calluses, corns, dry, scaling/flaking skin and keratoses. Specifically, when placed in a suitable carrier for dermatological use and applied regularly to the skin with or without occlusion, such proteinases and proteolytic enzymes selectively lyse hyperkeratotic tissue resulting in its softening, smoothing, thinning and exfoliation without harm to non-hyperkeratotic tissue. Such enzymes accomplish this by lysing only the 10-end peptide bonds of keratin protein, the dominant protein component of hyperkeratotic skin. These agents have minimal effect on normal skin because healthy epidermis lacks keratin, other than what exists in a fine layer of dead skin cells associated with normal sloughing. An example of an appropriate proteinase enzyme for the foregoing uses is Subtilisin Carlsberg manufactured as ALCALSE® Food Grade by Novo Corporation. Another example is a fungal protease/peptidase complex produced by submerged fermentation of a selected strain of *Aspergillus oryzae*, sold by Novo Corporation as FLAVOURZYME™ flavor enhancer.

Enzymes which digest proteins are widely distributed in nature. For example, U.S. Pat. No. 5,213,978 discloses extracellular proteases from *Micrococcus sedentarius* which are capable of solubilizing human callus material. However, the present invention employs proteolytic enzymes that selectively desquamify hyperkeratotic mammalian tissue. Tests conducted under bilateral, placebo-controlled, double blind conditions evidenced no irritation to adjacent normal skin and a 50% reduction in hardness and density within 14 days of nightly application to foot callus.

Selective desquamification of callus, corn and keratoses is possible because normal skin lacks the proteins containing 10-end peptide bonds which are broken by proteolytic enzymes. Products currently employed to treat callus, corns, keratoses and dry skin generally contain acids which can irritate normal skin and can cause burns of healthy tissue which can lead to infection.

OBJECTS OF THE INVENTION

The present invention provides several unique advantages over the prior art.

The present invention provides novel compositions for treatment of hyperkeratotic mammalian tissue said compositions containing known proteolytic enzymes originally developed for the hydrolysis of food-related proteins wherein these novel compositions containing these proteinases safely soften, thin and exfoliate hyperkeratotic formations on the skin, including calluses, corns, dry, scaling/flaking skin and keratoses.

The present invention further provides methods for administering novel compositions containing proteolytic enzymes for treatment of hyperkeratotic mammalian tissue.

The present invention still further provides novel compositions for exfoliating hyperkeratotic mammalian tissue at body temperature and at neutral pH.

The present invention further provides a method for administering proteolytic enzymes in a suitable carrier for dermatological use and applied regularly to the skin with or without occlusion, wherein such proteolytic enzymes selectively lyse hyperkeratotic tissue resulting in its softening, smoothing, thinning and exfoliation without harm to non-hyperkeratotic tissue.

DETAILED DESCRIPTION OF THE PREFERRED EMBODIMENTS

The present invention will be better understood by the following detailed description of the invention and with reference to the figures.

The novel compositions of the present invention comprise proteinases or proteolytic enzymes in a suitable carrier for dermatological use. An example of an appropriate proteolytic enzyme for this use is Subtilisin Carlsberg manufactured as ALCALASE® Food Grade by Novo Corporation. Subtilisin Carlsberg is an endopeptidase produced by submerged fermentation of a selected strain of *Bacillus licheniformis*. The main enzyme component, Subtilisin A (=Subtilisin Carlsberg), is an endoproteinase extensively described in literature. Table 1 summarizes some of the biochemical properties of the proteinase in ALCALASE®. The optimal conditions for ALCALASE® are temperatures between 55° C. (131° F.) and 70° C. (158° F.), depending on the type of substrate, and pH values between 6.5 and 8.5.

TABLE 1

| | ALCALASE ® |
|---|---|
| Generic Name | Subtilisin Carlsberg |
| Type of action | Endopeptidase |
| Nature of catalytic site | Serine |
| Inhibition by: | |
| DFP & PMSF1) | + |
| EDTA2) & phosphate | 0 |
| Soya bean trypsin inhibitor | 0 |
| Bonds attacked in the oxidized B-chain of insulin3) | 4–5, 9–10, 11–12, 15–16, 26–27 |
| Molecular weight (approx.) | 27,300 |

1)DFP = Di-isopropyl flouorophosphate, PMSF = Phenylmethylsulphonylfluoride
2)EDTA Ethylenediamine tetra-acetic acid
NH2-Phe-Val-Asn-Gln-His-Leu-CySO3H-Gly-Ser-His-Leu-Val-Glu-Ala-Leu-
1 5 10 15
Tyr-Leu-Val-CySO3H-Gly-Glu-Arg-Gly-Phe-Phe-Tyr-Thr-Pro-Lys-Ala
17 20 25 30
(from Johansen, J.T. et al, C.R. Trav. Lab. Carlsberg 36,365–384, 1968)

ALCALASE® Food Grade is standardized in Anson Units per g (AU/g).
ALCALASE® 2.4 L . . . Declared activity: 2.4 AU/g The proteolytic activity is determined according to an analytical standard using the DMC method.

ALCALASE® 2.4 L is a dark-brown liquid and is readily soluble in water at all concentrations. The color may vary from batch to batch and color intensity is not an indication of product strength.

Activity

Figure 1:
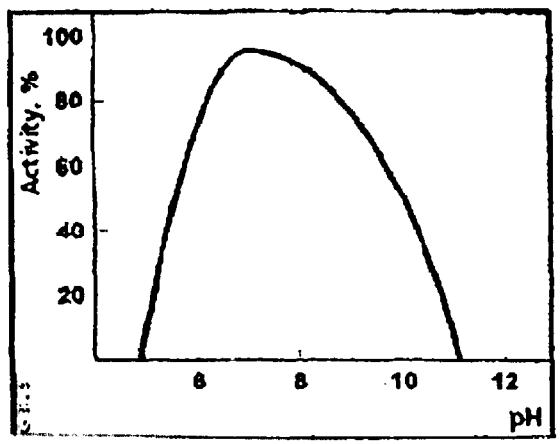
FIG. 1 is a graphical representation of the influence of pH on the activity of one of the proteolytic enzymes of the present invention.
Figure 2:
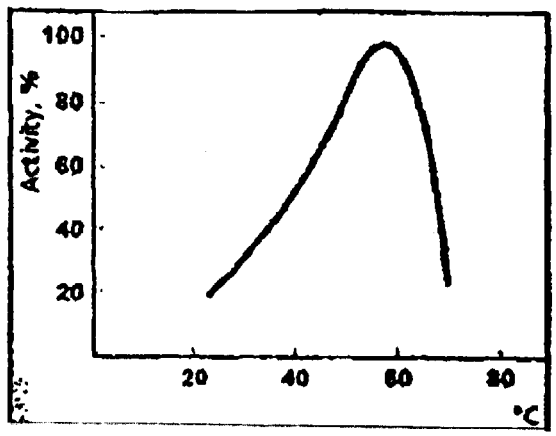
FIG. 2 is a graphical representation of the influence of temperatures on the activity of one of the proteolytic enzymes of the present invention.

By analyzing ALCALASE® at various pH values using a modified Anson/haemoglobin method, its optimum activity has been found to be at a pH of between 6.5 and 8.5 (FIG. 1). Similarly, under analytical conditions ALCALASE® shows good activity (about 40%) at normal human body temperature (37° C.). ALCALASE® has its temperature optimum around 60° C. (140° F.) (FIG. 2).

Figure 3:
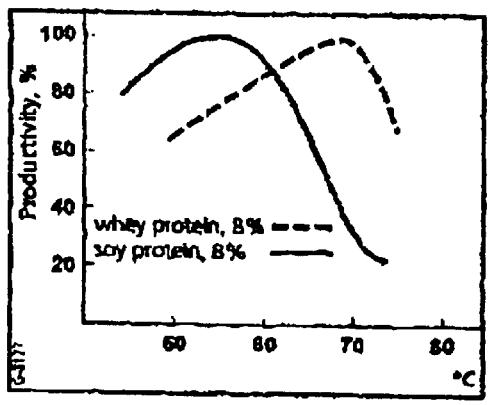
FIG. 3 is a graphical representation of the productivity of one of the proteolytic enzymes of the present invention.

FIG. 3 illustrates the productivity of ALGALASE® at various temperatures on the substrates whey protein and soya protein, respectively. The productivity is depicted in relative values. DH is defined as percentage of peptide bonds cleaved.

ALCALASE® can be inactivated in 30 minutes at 50° C. (122° F.) or higher when the pH is 4, and in 10 minutes at 85° C. (185° F.) or higher when the pH is 8. However, the inactivation is very much dependent on the substrate (substrate concentration, pH, etc.).

Another example of a suitable proteolytic enzyme is one marketed under the name FLAVOURZYME™ as a flavor enhancer. FLAVOURZYME™ sold by Novo Corporation, is a fungal protease/peptidase complex produced by submerged fermentation of a selected strain of Aspergillus oryzae. This proteolytic enzyme has both endoprotease and exopeptidase activities. FLAVOURZYME™ is currently used as an aid in food processing to debitter bitter protein hydrolysates and to increase hydrolysis of food proteins to enhance flavor development.

The optimal pH for the enzyme complex is in the range of 5.0–7.0. The optimal pH for the exopeptidase is approx. 7.0, as determined by application trials. The optimal pH for debittering is also approx. 7.0. The optimal temperature for the enzyme complex as well as the exopeptidase is around 50° C. (122° F.).

FLAVOURZYME™ is standardized in Leucine Amino Peptidase Units per gram (LAPU/g).

| | |
|---|---|
| FLAVOURZYME ™ 500 MG | Declared activity: 500 LAPU/g |
| FLAVOURZYME ™ 500 L | Declared activity: 500 LAPU/g |

One LAPU is the amount of enzyme which hydrolyzes 1 pmol of L-leucine-p-nitroanilide per minute. FlAVOURZYME™ is available as FLAVOURZYME™ 500 L, a liquid product, and FLAVOURZY™ 500 MG, a brown, free-flowing, non-dusting microgranulate granulated on NaCl. The color may vary from batch to batch and color intensity is not an indication of product strength. FLAVOURZYME™ 500 MG and FLAVOURZYME™ 500 L are both readily soluble in water.

Figure 4:
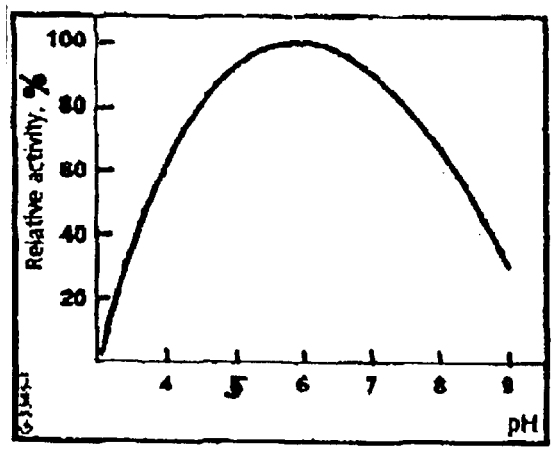
FIG. 4 is a graphical representation of the influence of pH on the activity of one of the proteolytic enzymes of the present invention.
Figure 5:
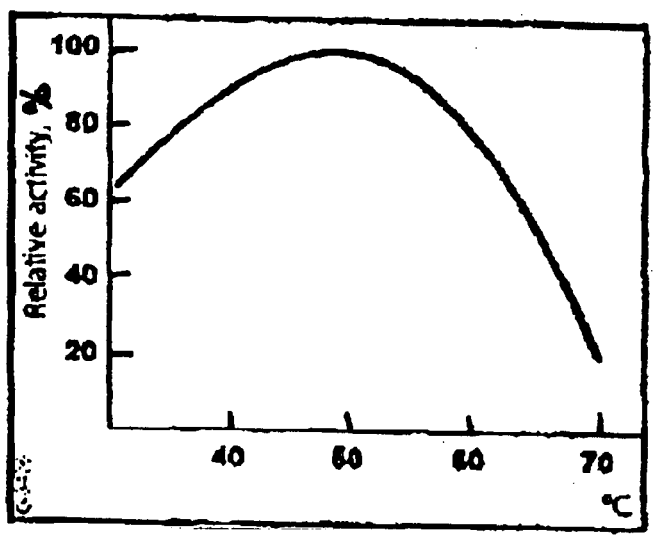
FIG. 5 is a graphical representation of the influence of temperatures on the activity of one of the proteolytic enzymes of the present invention.

The activity of FLAVOURZYME™ varies with pH and temperature as can be seen in FIGS. 4 and 5.

FLAVOURZYME™ can be inactivated in 10 minutes at 75° C. (167° F.) or higher. However, the inactivation is very much dependent on the substrate (substrate concentration, pH, etc.).

Preferably the compositions of the present invention are in the form of pharmaceutical or cosmetic preparations for topical application such as solutions, creams, ointments, ointment sticks, gels, powders or adhesive plasters. The proteolytic enzymes are optimally carried in any pharmaceutically or cosmetically acceptable carrier such as but not limited to petrolatum, water-based creams or lotions, oil-based creams or lotions and other known agents for exfoliation provided that the resulting mixture maintains a neutral or alkaline pH, as the enzymes become inactive in an unduly basic or acid environment.

Such topical compositions may contain other active pharmaceutical ingredients such as fungicides and antibiotics as well as conventional additives such as fragrance and other cosmetic additives and excipients commonly used in cosmetic and dermatology products invention.

It has been discovered that compositions containing from about 1% to about 15% proteolytic enzymes in a pharmaceutically acceptable carrier are effective for softening, thinning and removing hyperkeratotic mammalian tissue. The pharmaceutically acceptable carrier is present in an amount of about 85% to about 99%. In a preferred embodiment the composition contains from about 2.4% to about 10% proteolytic enzymes, depending on the application. The remainder of the composition comprises a pharmaceutically acceptable carrier in an amount from about 90% to about 97.5%.

The composition may contain other additives or excipients such as but not limited to antibiotics, fungicidal agents, anesthetics, moisturizers, fragrance, dye, etc.

The following examples of compositions containing the aforementioned proteases are preferred embodiments of the present invention:

Formula #1: A composition comprising 5% proteolytic enzymes and 95% petrolatum, wherein, for example, ALCALASE® constitutes 90% of the enzyme component and FLAVOURZYME™ 10%. This formula is appropriate for application anywhere on the human body, excluding the face and genital regions.

Formula #2: A composition comprising 2.4% proteolytic enzymes and 97.5% petrolatum wherein, for example, ALCALASE® constitutes 90% of the enzyme component and FLAVOURZYME™ 10%. This formula is appropriate for facial application, particularly near delicate areas such as the eyes, nose and mouth.

Formula #3: A composition comprising 10% proteinase enzymes comprising ALCALASE® and/or FLAVOURZYME™ and 90% petrolatum for use on mammalian skin under veterinarian care.

The protease-containing composition is preferably applied to callused areas, corns, keratoses or dry cracked skin every 12 hours and optionally covered with a dressing. Between applications the area is washed with a warm, wet washcloth and soap using a firm rubbing action. For sole callus, applications are preferably reduced to three times weekly when the callus no longer causes discomfort, as some padding is important for bone protection. Likewise, once the hyperkeratotic condition is exfoliated, periodic use of the ointment serves to prevent buildup or recurrence.

In preferred embodiment the invention comprises the composition of the present invention disposed on a carrier such as a dressing such as but not limited to an adhesive tape, plaster or the like.

In a most preferred embodiment a dressing such as but not limited to an adhesive bandage is impregnated with the protease containing composition of the present invention. Preferably the dressing comprises an adhesive bandage with an absorbent pad, said pad impregnated with the protease and a pharmaceutically or cosmetically acceptable carrier, such as but not limited to petrolatum. The composition-impregnated dressing is then applied over the hyperkeratotic tissue to be treated.

Experiments

Figure 6:
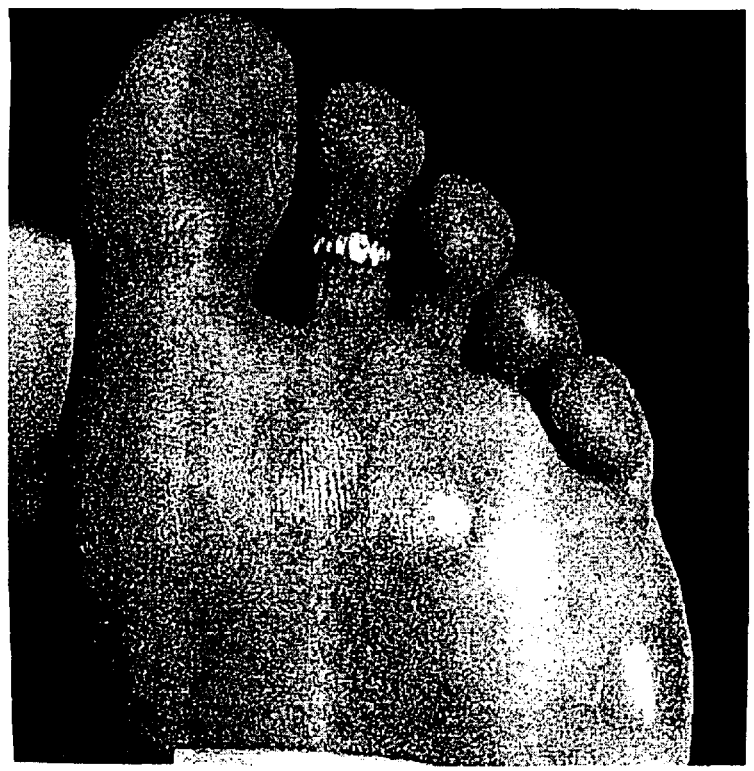
FIG. 6 is a photograph of the sole of a foot of a patient prior to treatment according to the teachings of the present invention.
Figure 7:
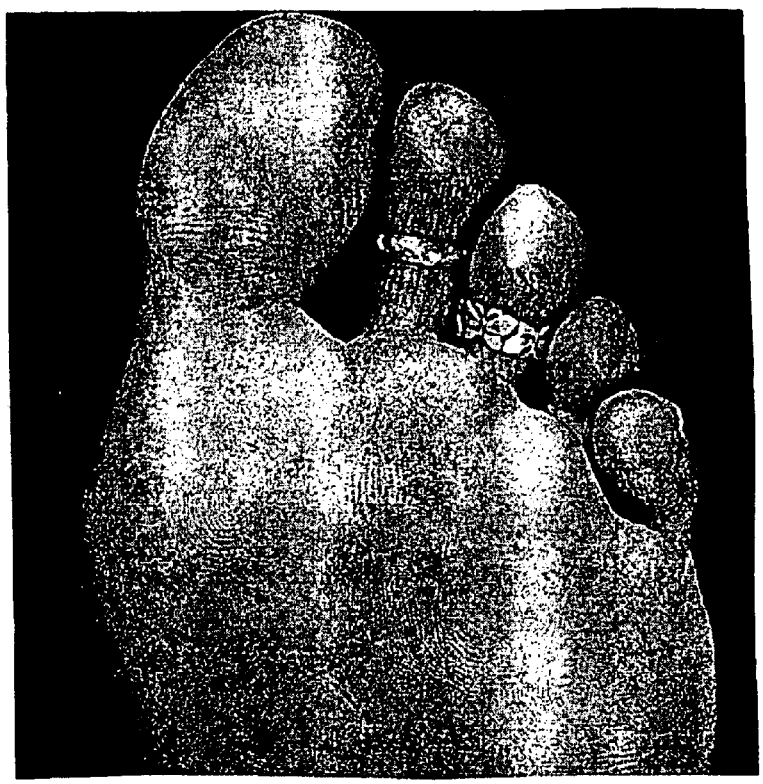
FIG. 7 is a photograph of the sole of a foot of the patient according to FIG. 6 after treatment according to a preferred embodiment of the present invention.

Experiment 1:

In a 21-day, placebo-controlled study of sole callus using Formula #1, resulted in rapid improvement in walking comfort for all participants within 14 days as exemplified by the photographs of FIGS. 6 and 7. An independent clinical investigator reported 50% less callus than obtained from available callus lotions, creams and ointments.

Figure 8:
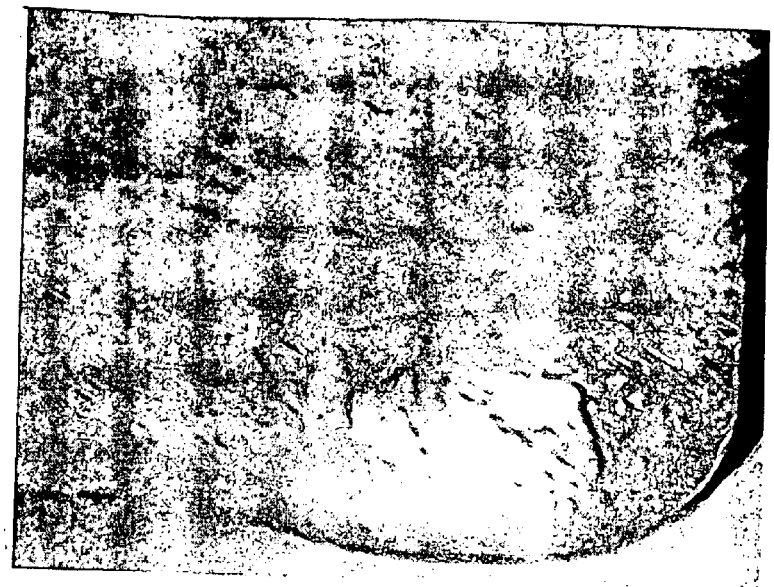
FIG. 8 is a photograph of the heel of a foot of a patient prior to treatment according to the teachings of the present invention.
Figure 9:
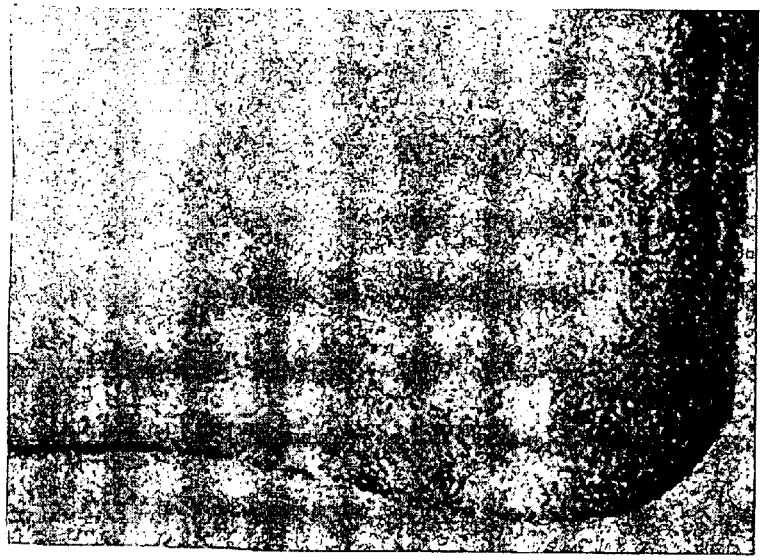
FIG. 9 is a photograph of the heel of a foot of the patient according to FIG. 8 after treatment according to a preferred embodiment of the present invention.

Experiment 2: An 81-year-old man with severe heel dryness, included cracked and peeling skin, applied Formula #1 to his heel and removed all hyperkeratotic tissue within 10 days as exemplified in the photographs of FIGS. 8 and 9.

Experiment 3: A 50-year-old male using Formula #1 exfoliated his heel fissures after two weeks of daily applications. He continued to maintain fissure-free heels with 2 or 3 times weekly application. Heel fissures were also similarly removed on a young male.

Experiment 4: A 45-year-old female applied Formula #1 to her thick and flaking sole margins which were cracked and dry to the touch. With regular use, the edges of her soles became soft and smooth.

Experiment 5: A middle-aged female used Formula #1 to remove keratoses from the top of her feet by applying the ointment twice daily for seven days. In addition her sole calluses were alleviated.

Experiment 6: A 57-year-old female used Formula #1 to remove calluses from her hands acquired from gardening. Within one day the calluses on her palm were 50% reduced. Within three days, the callused areas appeared normal.

Experiment 7: A middle-aged female applied Formula #1 to corns on her toes. Sufficient softening was noted in 48 hours to eliminate shoe discomfort. The corn's surface layers were lifted mechanically and peeled off after 4 days.

While the invention has been described by reference to specific embodiments, this is for illustrative purposes only. Various modifications to the above invention will become apparent to those skilled in the art, all of which are intended to fall within the spirit and scope of the present invention. All patents and publications referred to herein are hereby incorporated by reference.

What is claimed is:

1. A composition for the removal, softening or thinning of hyperkeratotic mammalian tissue comprising at least one food-grade proteolytic enzyme and a pharmaceutically or cosmetically acceptable carrier, said at least one food-grade proteolytic enzyme selected from the group consisting of Subtilisin Carlsberg and a fungal protease/peptidase complex produced by submerged fermentation of a selected strain of *Aspergillus oryzae*.

2. The composition according to claim 1 said food-grade proteolytic enzyme comprising Subtilisin Carlsberg and a fungal protease/peptidase complex produced by submerged fermentation of a selected strain of *Aspergillus oryzae*.

3. The composition according to claim 1 said pharmaceutically or cosmetically acceptable carrier comprising a water-based carrier.

4. The composition according to claim 1 said pharmaceutically or cosmetically acceptable carrier comprising an oil-based carrier.

5. The composition according to claim 1 further comprising fragrance.

6. The composition according to claim 1 further comprising an antibiotic agent.

7. The composition according to claim 1 further comprising an antifungal agent.

8. The composition according to claim 1 further comprising an anaesthetic.

9. The composition according to claim 1 said pharmaceutically or cosmetically acceptable carrier comprising petrolatum.

10. The composition according to claim 1 comprising from about 1% to about 15% proteolytic enzyme and from about 85% to about 99% pharmaceutically or cosmetically acceptable carrier.

11. The composition according to claim 1 comprising about 5% proteolytic enzyme and about 95% petrolatum.

12. The composition according to claim 11 said proteolytic enzyme comprising about 90% Subtilisin Carlsberg and about 10% fungal protease/peptidase complex produced by submerged fermentation of a selected strain of *Aspergillus oryzae*.

13. The composition according to claim 1 comprising about 2.4% proteolytic enzyme and about 97.5% petrolatum.

14. The composition according to claim 11 said proteolytic enzyme comprising about 90% Subtilisin Carlsberg and about 10% fungal protease/peptidase complex produced by submerged fermentation of a selected strain of *Aspergillus oryzae*.

15. The composition according to claim 1 comprising about 10% proteolytic enzyme and about 90% petrolatum.

16. The composition according to claim 13 said proteolytic enzymes comprising Subtilisin Carlsberg and/or a fungal protease/peptidase complex produced by submerged fermentation of a selected strain of *Aspergillus oryzae*.

17. A method for treating hyperkeratotic mammalian tissue comprising the steps of:
    obtaining a composition comprising at least one food grade proteolytic enzyme selected from the group Subtilisin Carlsberg and a fungal protease/peptidase complex produced by submerged fermentation of a selected strain of *Aspergillus oryzae* and a pharmaceutically or cosmetically acceptable carrier, and applying said composition to said hyperkeratotic tissue.

18. The method according to claim 17 comprising applying said composition to callus.

19. The method according to claim 17 comprising applying said composition to a corn.

20. The method according to claim 17 comprising applying said composition to follicular keratosis.

21. The method according to claim 17 comprising applying said composition to dry or cracked skin.

22. The method according to claim 17 comprising the further step of covering with a dressing said tissue to which said composition has been applied.

23. A dressing for the treatment of hyperkeratotic mammalian tissue comprising a substrate, at least one food-grade proteolytic enzyme, and a pharmaceutically or cosmetically acceptable carrier, said proteolytic enzyme and carrier disposed on said substrate.

* * * * *